United States Patent
Von Der Haar

(10) Patent No.: US 6,320,929 B1
(45) Date of Patent: Nov. 20, 2001

(54) METHOD FOR SCANNING AN EXAMINATION SUBJECT WITH A CT DEVICE

(75) Inventor: Thomas Von Der Haar, Nuremberg (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/500,025

(22) Filed: Feb. 8, 2000

(30) Foreign Application Priority Data

Feb. 12, 1999 (DE) .............................................. 199 05 974

(51) Int. Cl.⁷ ...................................................... A61B 6/03
(52) U.S. Cl. ................................. 378/4; 378/15; 378/901
(58) Field of Search ................................. 378/4, 901, 145, 378/147, 148, 149, 150, 19, 15

(56) References Cited

U.S. PATENT DOCUMENTS

| | | | |
|---|---|---|---|
| 4,324,978 | * 4/1982 | Kalender et al. | 378/4 |
| 5,684,855 | * 11/1997 | Aradate et al. | 378/4 |
| 5,724,400 | * 3/1998 | Swerdloff et al. | 378/65 |
| 5,815,546 | * 9/1998 | Flohr et al. | 378/4 |
| 6,173,033 | * 1/2001 | Klingenbeck-Regn et al. | 378/20 |
| 6,173,039 | * 1/2001 | Hampel et al. | 378/150 |
| 6,233,308 | * 5/2001 | Hsieh | 378/901 |
| 6,236,707 | * 5/2001 | Flohr et al. | 378/15 |

FOREIGN PATENT DOCUMENTS

OS 197 48 891  6/1998 (DE).
OS 197 21 535  11/1998 (DE).

* cited by examiner

*Primary Examiner*—Drew Dunn
(74) *Attorney, Agent, or Firm*—Schiff Hardin & Waite

(57) ABSTRACT

In a method for scanning an examination subject and a CT (computed tomography) device for implementing the method, the cross-section of the X-ray beam emanating from the X-ray source of the device is modified during the scan so that, at all times, substantially only the region of the examination subject that is used for the reconstruction of images is penetrated by the X-ray beam.

19 Claims, 3 Drawing Sheets

METHOD FOR SCANNING AN EXAMINATION SUBJECT WITH A CT DEVICE

BACKGROUND OF THE INVENTION

1. Field of the Invention

The present invention is directed to a method for scanning an examination subject with a CT (computed tomography) device and to a CT device for implementing the method. The CT device is of the type having an X-ray source that emits an X-ray beam, and a detector system composed of several rows of detector elements on which the beam is incident, the X-ray beam being displaceable relative to a system axis, and the detector signals that are formed in the various projections being fed to a computer, which constitutes images of the examination subject therefrom.

2. Description of the Prior Art

Known radiographic CT devices have an X-ray source that directs a collimated pyramidal X-ray beam through the examination subject, for instance a patient, onto a detector system that is constructed of a two-dimensional array of detector elements, which is completely irradiated by the X-ray source. The X-ray source and, depending on the construction of the radiographic CT device, the detector system as well, are attached on a gantry that rotates around the examination subject. A support table for the examination subject can be moved, relative to the gantry. The longitudinal position from which the X-ray beam penetrates the examination subject and the angle at which the X-ray beam penetrates the examination subject are continuously modified as a consequence of the rotation of the gantry and this relative movement. Every detector element of the detector system that is struck by X-rays produces a signal, which represents a measure of the total transparency of the body of the examination subject for the X-rays emanating from the X-ray source on its path to the detector system. The set of output signals of the detector elements of the detector system that is obtained for a particular angular position of the X-ray source is referred to as a projection. A scan comprises a set of projections which are obtained at different positions of the gantry and/or at different positions of the support table. The radiographic CT device picks up a number of projections during one scan, in order to be able to construct a two-dimensional tomogram of a slice of the examination subject. Several slices can be picked up at once by the detector system that is formed by several detector rows.

Larger volumes of the examination subject are usually picked up by sequential scanning or spiral scanning.

In sequential scanning, the data are picked up during the rotational movement of the gantry, while the examination subject is situated in a fixed position, and so a plane slice is scanned. Between scans of consecutive slices, the examination subject is moved into a new position, in which the next slice can be scanned. This process is continued until all slices that were specified prior to the examination have been scanned.

In spiral scanning the gantry with the X-ray source rotates continuously around the examination subject, while the support table and the gantry are continuously displaced relative to one another along a system axis. The X-ray source thus describes a spiral (helical) path in relation to the examination subject, until the volume that was specified prior to the examination has been scanned. Images of individual slices are then computed from the spiral data obtained in this manner.

In conventional radiographic CT devices, the cross-section of the X-ray beam is set by means of a radiation diaphragm at the source prior to the scanning of an examination subject and is not modified during this scan (German OS 197 21 535). Because of this, regions of the examination subject that are not used for image reconstruction are frequently penetrated by X-rays, particularly in CT devices with a multiline detector system. This is also true of a radiographic CT system as taught in German OS 197 48 891, in which it is possible to modify the slice thickness during the scan according to the body region of the examination subject currently being scanned.

SUMMARY OF THE INVENTION

An object of the present invention is to provide a method of the above type so as to prevent the application of a radiation dose in the region of the examination subject from which images are not reconstructed.

This object is inventively achieved in a method for scanning an examination subject and to a CT device wherein an X-ray source of the CT device emits an X-ray beam and wherein the beam is incident on a detector system of the CT device composed of several rows of detector elements (detector rows), the X-ray beam being displaced relative to a system axis for purposes of scanning the examination subject, and wherein detector signals that are formed for different projections in the scanning of the examination subject are fed to a computer, which reconstructs images of the examination subject therefrom; and wherein the cross-section of the X-ray beam is modified during the scan such that at all times substantially only the region of the examination subject that is used for the reconstruction of images is penetrated by the X-ray beam.

In the inventive method for scanning an examination subject, it is advantageous that the application of unused radiation dosage is prevented, above all in the margin regions of the examined volume. This is easily accomplished by a radiation diaphragm at the source side, the cross section of which is varied in the course of the scan such that the X-ray beam, being so gated, only penetrates the region of the examination subject from which measurement data that can be evaluated for the image reconstruction are acquired.

To achieve this, it is necessary to set the aperture of the radiation diaphragm at the source side so as to be intermittently asymmetric to the center of the detector system, which is not typical.

In an embodiment of the invention, the slice diaphragm that is already present in conventional CT devices is used as the radiation diaphragm at the source side.

According to another embodiment of the invention, the application of unused radiation dosage is prevented by, during the scan, continuously adapting the cross-section of the X-ray beam to the detector system such that at all times substantially only the detector elements of the detector system whose measurement data are used for image reconstruction are irradiated. This is accomplished by control of the radiation diaphragm at the tube side. In general, this diaphragm is opened so wide that the detector system is completely irradiated. Assuming a point focus of the X-ray source, the region of the examination subject situated within the pyramid situated between the focus and the edges of the detector system are thus penetrated by the X-radiation.

The adaptation of the x-ray beam to the detector system inventively occurs specifically by, during the scan, fading or occluding (blanking out) respective individual rows of the detector system. That is, by adjustment of the radiation diaphragm at the tube side, the cross-section of the X-ray beam is so varied during the scan so that only a part of the detector system is irradiated in an intermittent manner. This is detailed below with in the context of examples of spiral and sequential scans.

In a spiral scan there are regions at the beginning and end of a scan that are covered by only a part of the detector rows. The measurement data of the detector elements that are acquired in these regions either are not used for image reconstruction, or they lead to images having diminished image quality compared to images from the middle scan region. These images are generally unusable for diagnostic purposes and therefore are discarded.

The dose of X-radiation that is applied to the examination subject therefore can be used only partly for reconstructing images in conventional radiographic CT devices. The portion of unused dosage increases in spiral scanning with the number of detector rows and with decreasing pitch (shift of the support mechanism per 360° revolution of the radiation source (full revolution) around the examination subject, in relation to the extent of a detector element in the z-direction). In short spiral scans this unused portion can amount to a large part of the total applied dose. For example, for a three-row detector system, given 10 spiral revolutions with a pitch of 1, this unused portion is 20% as computed by the formula:

$$D_{rel} = \frac{1}{N}\left(\frac{n}{p} - 1\right)$$

wherein $D_{rel}$ is the relative portion of the unused dose; N is the number of spiral revolutions; n is the number of detector rows; and p is the pitch.

When a spiral scan is executed, the cross-section of the radiation diaphragm at the tube side is inventively set at the beginning of the CT scan such that only that detector row is irradiated which is farthest back with respect to the direction of motion of the support table along the system axis relative to the X-ray source (z direction). All remaining rows are blanked out, and thus the applied radiation dose is reduced accordingly. Later in the course of the scan the remaining detector rows are faded in row-by-row depending on the pitch, such that only those rows are irradiated which deliver measurement data from a region of the examination subject that is used for image reconstruction. This avoids irradiation of regions of the examination subject that are not covered by all detector rows in the course of the spiral scan, and so could be rendered in the image reconstruction only with reduced quality.

Analogously, at the end of the spiral scan the rear detector rows in the z-direction are gradually blanked out, so that the region of the examination subject that is to be reconstructed is still covered by all detector rows, and regions of the examination subject situated adjacently in z-direction are no longer irradiated.

In the spiral scan, the time and location for fading the detector rows out or in, respectively, is dependent on the pitch. Given a pitch of 1 (i.e. the forward displacement of the support table per 360° revolution of the X-ray source (complete revolution) around the examination subject corresponds to the width of one detector row), an additional detector row is faded in with each complete revolution of the X-ray source and, consequently, an additional detector row is blanked out at the end of each complete revolution. Given a higher pitch, the rows can be faded in or out, respectively, more rapidly; for example, one row per half-revolution given a pitch of 2. Conversely, given a pitch of 0.5, only one detector row can be additionally faded in or out, respectively, every other 360° revolution.

In the sequential scan, the inventive method is particularly advantageous when the region of the examination subject that is to be reconstructed does not conform to a whole-number multiple of the region that can be detected by the detector system during one sequence, because in this case, as well, the examination subject is conventionally subjected to a radiation dose that is not incident on an active detector element and consequently does not contribute to the imaging.

To prevent this, a portion of the detector rows is inventively blanked out at times, so that substantially only the region that is to be reconstructed is irradiated. The blanking out of one or more rows is preferably accomplished at the beginning or end of the sequential scan, but the blanking out also can occur in the middle of a scan. Ultimately one or more rows can be blanked out in all the sequential pick-ups or in some of the sequential pick-ups. The aim is always to bring the irradiated region into conformity with the region that is to be reconstructed.

The detector rows that are not used for the image reconstruction can be inventively blanked out, or respectively, the detector rows that are used for the image reconstruction can be faded in, in a continuous manner. Preferably, however, the X-rays are gated out or in, respectively, by a diaphragm such that the detector rows that are blanked out or faded in, respectively, are blanked out or faded in completely in an optimally short time. In this way, the radiation dose is minimized, since the detector signal of a partially gated detector row generally cannot be used for image reconstruction.

DESCRIPTION OF THE PREFERRED EMBODIMENTS

Figure 1:
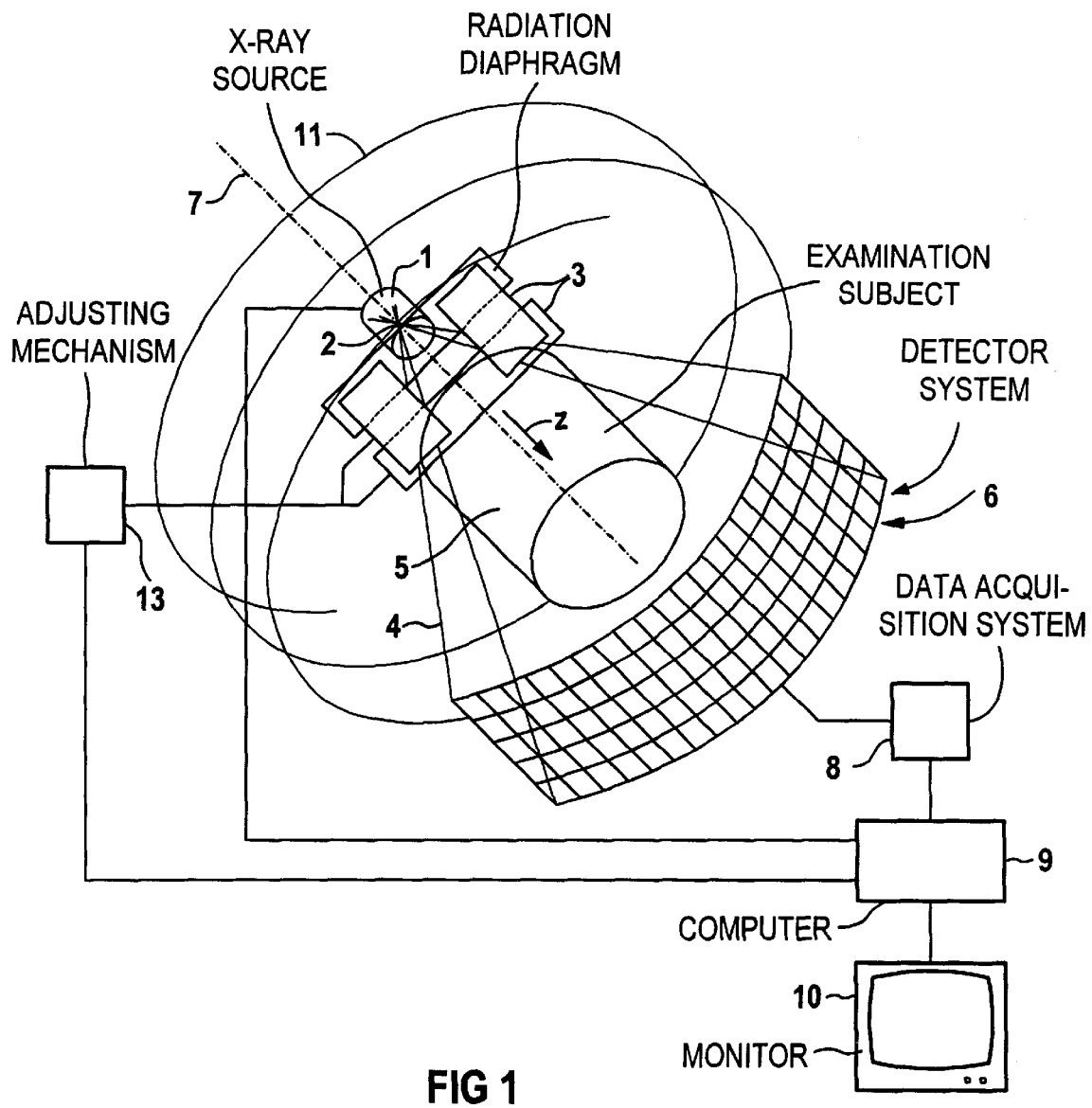
FIG. 1 is a schematic illustration of a CT device having a multiline detector system implementing the inventive method.

FIG. 1 is a schematic illustration of a CT device that is provided for implementing the inventive method, which has an X-ray source 1, for instance an X-ray tube, with a focus 2 from which a pyramidal X-ray beam 4 emanates, which is gated by a radiation diaphragm 3 at the source side (that is, the tube side) and which penetrates an examination subject 5, for instance a patient, and is incident on a detector system 6. The detector system 6 is composed of several parallel detector rows, each of which has a number of detector elements. The X-ray source 1 (or at least the focus 2 thereof) and the detector system 6 form a measuring system that can be displaced around a system axis 7 and moved along the system axis relative to the examination subject 5, so that the examination subject is penetrated at different projection angles α and different z-positions along the system axis 7. From the output signals of the detector elements of the detector system 6 which thereby result, a data processing system 8 generates measurement values, which are fed to a computer 9 that calculates an image of the examination subject 5, which is reproduced on a monitor 10.

The radiographic CT device depicted in FIG. 1 can be used for both sequential and spiral scans.

In sequential scanning, the examination subject 5 is scanned slice-by-slice. The X-ray source 1 (or the focus 2 thereof) is displaced around the examination subject 5 relative to the system axis 7, and the measurement system 1,6 picks up a number of projections in order to be able to construct a two-dimensional tomogram of a slice of the examination subject 5. Between the scanning of consecutive slices, the examination subject 5 is moved into a new z-position. This process is repeated until all slices that include the area to be reconstructed are covered.

During a spiral scan, the measuring system 1,6 moves relative to the examination subject 5 on the spiral path 11 in a continuous manner, until the region that is to be reconstructed is covered completely. A volume dataset is generated in this process. The computer 9 calculates a planar dataset therefrom using an interpolation method, from which dataset the desired images can be reconstructed as in the sequential scan.

FIG. 1 depicts an operating state in which the X-ray beam 4 emanating from the X-ray source 1 is gated such that the detector system 6 is irradiated over a desired width in z-direction, the entire width in this case. In conventional CT devices, this setting is maintained during the entire scan.

Figure 2:
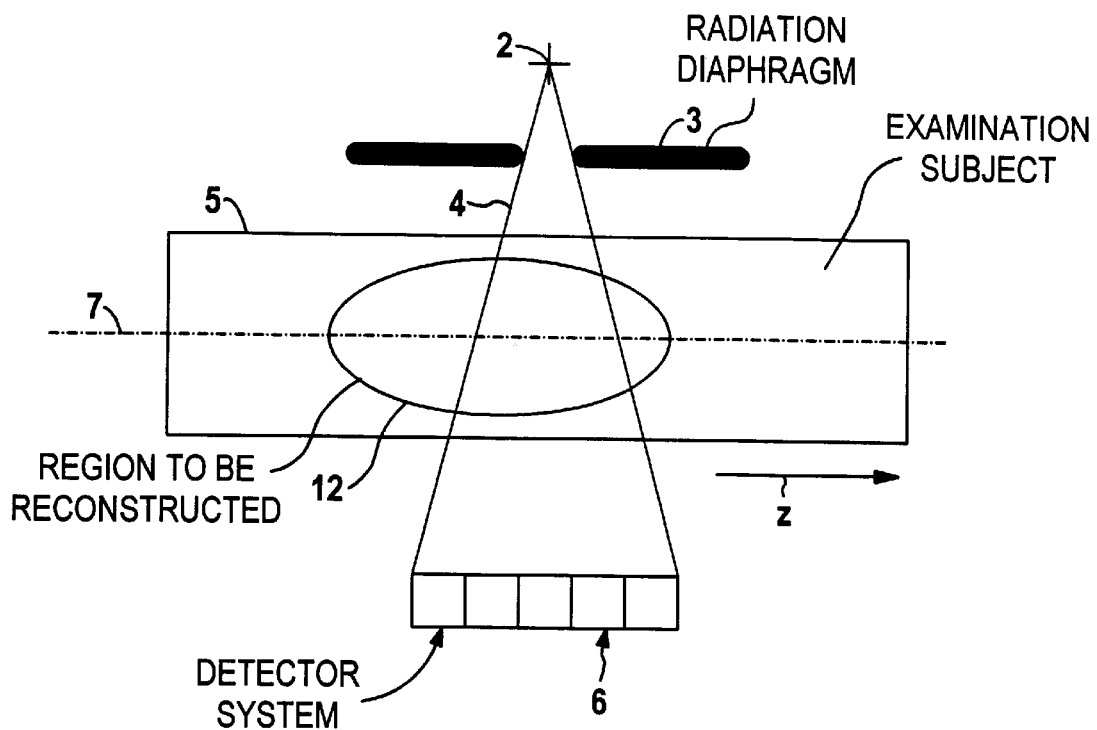
FIG. 2 is a schematic diagram of the radiation geometry of the CT device according to FIG. 1 for the operating state illustrated by FIG. 1.

FIG. 2 again depicts the radiation geometry for the operating state of a CT device having a multiline detector system as illustrated in FIG. 1, in a heavily simplified illustration. From the focus 2 of the X-ray source 1 (which is not illustrated in FIG. 2), an X-ray beam 4 emanates, which penetrates the examination subject 5 and is incident on the detector system 6. The radiation diaphragm 3 at the tube side is set such that the X-ray beam 4 irradiates the detector system 6 over its whole extent in the z-direction.

Figure 3:
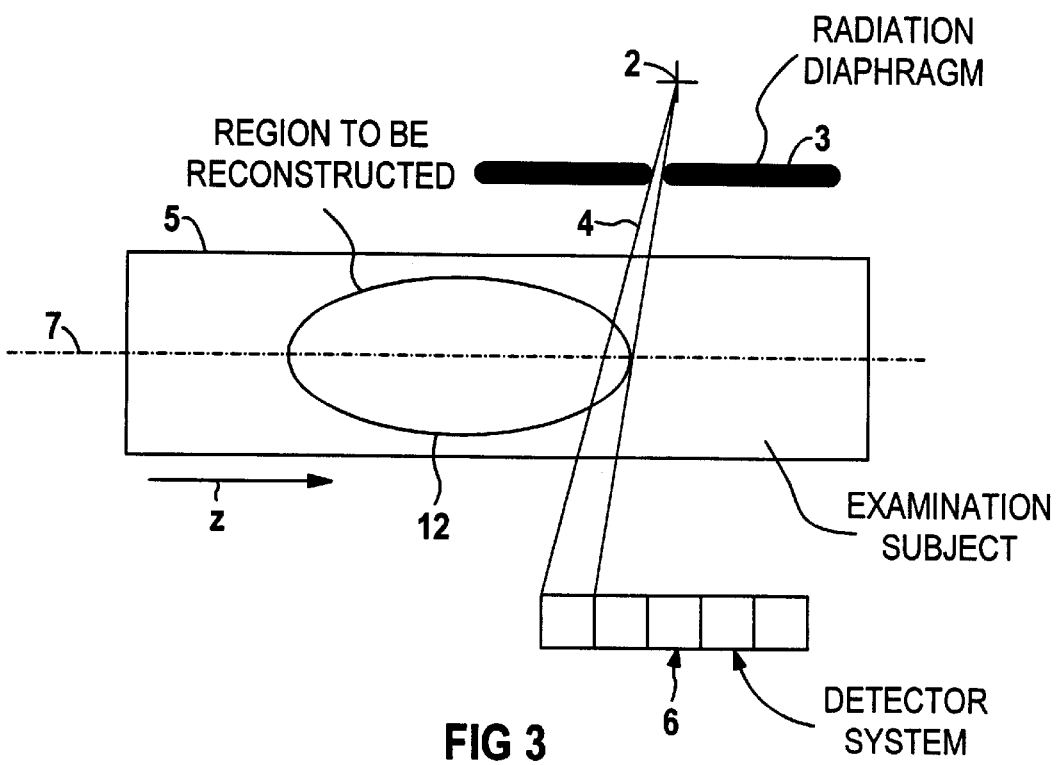
FIG. 3 is a schematic diagram of the radiation geometry of the CT device according to FIG. 1, at the beginning of a spiral scan that is conducted according to the inventive method.

At the beginning of the spiral scan, the radiation diaphragm 3 at the tube side is set in the manner illustrated in FIG. 3, so that only the region of the examination subject 5 that is covered by the row of detectors of the detector system 6 that is farthest back in the z-direction is penetrated by the X-ray beam 4. Assuming that the pitch is 1 (that is, the measuring system 1,6 moves the width of one detector row in the positive z-direction relative to the examination subject 5 with each 360° revolution around the examination subject), the cross-section of the radiation diaphragm 3 at the tube side is modified by means of an adjusting mechanism 13 (shown in FIG. 1) during the scan so that an additional row of detectors is faded in with each complete revolution, until all detector rows have been faded in.

Figure 4:
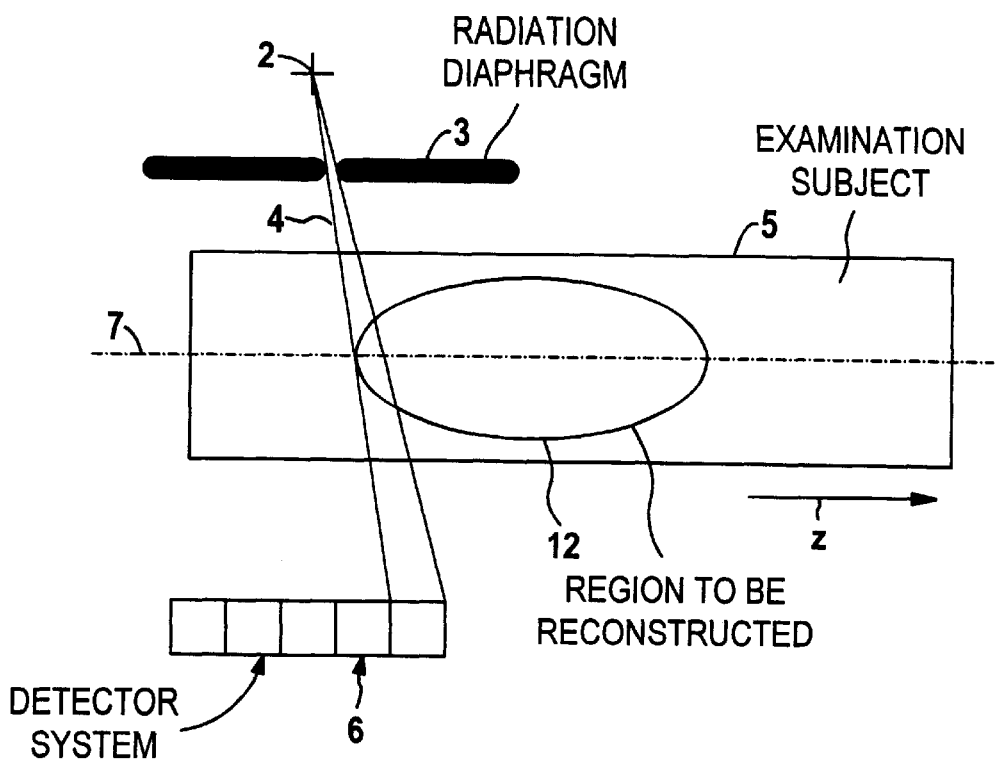
FIG. 4 is a schematic diagram of the radiation geometry of the CT device according to FIG. 1, at the end of a spiral scan that is conducted according to the inventive method.

The procedure at the end of a spiral scan differs from the procedure at the beginning of the spiral scan in that the cross-section of the radiation diaphragm at the tube side is modified by the adjusting mechanism 13 during the scan so that one detector row is blanked out with each complete revolution, until all detector rows have been blanked out. FIG. 4 illustrates an operating state at the end of a spiral scan in which all detector rows of the detector system 6 have been blanked out, with the exception of the frontmost in the z-direction. Given a pitch of 1, this detector row is also blanked out upon completion of a further revolution.

The invention is not limited with respect the pitch employed in the above-described exemplifying embodiment. For example, given a pitch of 0.5, a half-row can be blanked out or faded in, respectively, per complete revolution; given a pitch of 2, one row per half-revolution; given a pitch of 3, one row per one-third of a revolution, and so on.

By actuation of the adjusting mechanism 13 at the radiation diaphragm 3 at the tube side, the detector rows can be inventively blanked out or faded in, respectively, by rows, both continuously and abruptly. It is also possible for several rows of detectors to be blanked out or faded in, respectively, at the same time as a combined unit.

Figure 5:
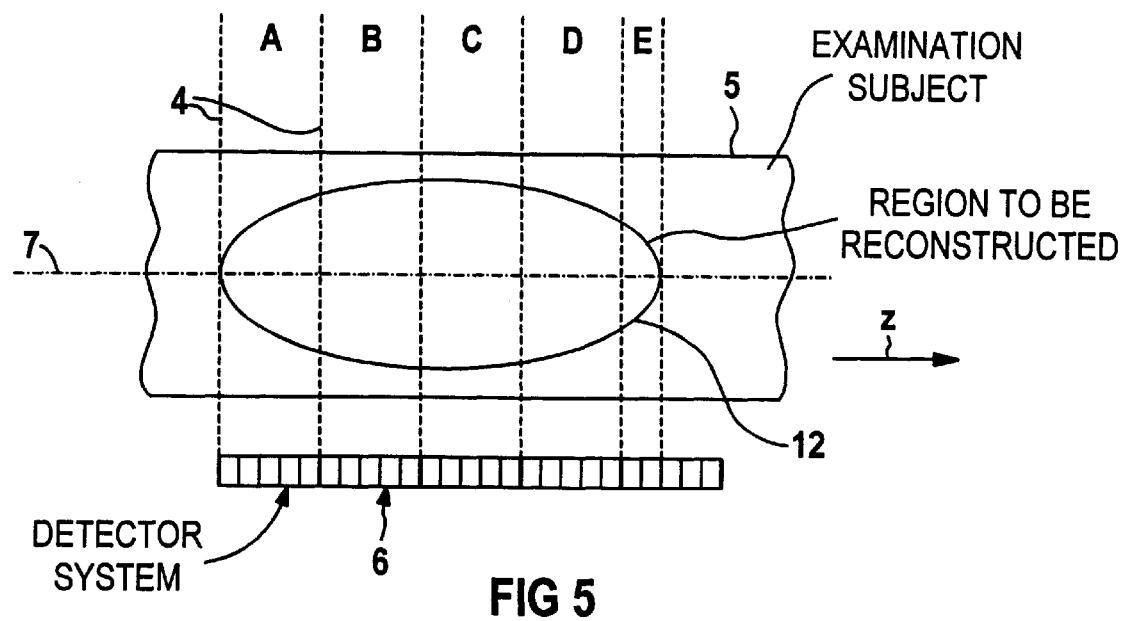
FIG. 5 is a schematic diagram of several sequences of a sequential scan that is conducted according to the inventive method.

In the exemplary embodiment according to FIG. 5, several sequences (A to E) of a sequential scan are illustrated. As can be seen from FIG. 5, the region 12 that is to be reconstructed does not conform to a whole-number multiple of the region that can be detected by the detector system 6 during one sequence. It is thus possible to modify the cross-section of the radiation diaphragm at the tube side in the last scan sequence E by means of the adjusting mechanism 13, so that the front rows of detectors in the z-direction are blanked out, but the region 12 that is to be reconstructed is still completely covered.

It is common to the exemplary embodiments according to FIGS. 3 to 5 that during the scan, the regions of the examination subject that are not needed for the reconstruction of images are substantially blanked out. This minimizes the radiation dose applied to the examination subject during the exam.

In the case of the described exemplary embodiments, the individual detector rows of the detector system 6 have the same width, as measured in the direction of the system axis 7, that is, in the z-direction. In the context of the invention, it is also possible to provide detector rows of varying widths.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for scanning an examination subject with a computed tomography device having an X-ray source with a focus from which an X-ray beam, having a beam cross section, emanates, and a detector system having a plurality of detector rows, each detector row containing a plurality of detector elements, and said computed tomography device having a system axis, said method comprising the steps of:

disposing an examination subject between said X-ray source and said detector system;

conducting a scan of said examination subject by displacing at least said focus of said X-ray source relative to said system axis to irradiate said examination subject with said X-ray beam from a plurality of different positions relative to said system axis;

generating detector signals with said detector system corresponding to radiation incident on said detector system during said scan;

supplying said signals to a computer and, in said computer, reconstructing an image of said examination subject from said detector signals; and modifying said cross section of said X-ray beam during said scan so that, at all times, substantially only a region of said examination subject which is used for reconstructing said image is penetrated by said X-ray beam.

2. A method as claimed in claim 1 comprising the additional step of providing a radiation diaphragm, having an adjustable aperture, at said X-ray source, and modifying said beam cross section, and wherein the step of modifying said beam cross section comprises modifying said beam cross section by adjusting a size of said aperture of said radiation diaphragm.

3. A method as claimed in claim 2 wherein said detector system has a center, and comprising the step of mounting said radiation diaphragm at said x-ray source so that said aperture of said radiation diaphragm is asymmetric relative to said center of said detector system.

4. A method as claimed in claim 1 wherein the step of modifying said beam cross section comprises at least one of blanking out a detector row from having said x-ray beam incident thereon during said scan and fading in a detector row to have said X-ray beam incident thereon during said scan.

5. A method as claimed in claim 4 comprising the additional step of providing a radiation diaphragm, having an adjustable aperture, at said X-ray source, and modifying said beam cross section, and wherein the step of modifying said beam cross section comprises modifying said beam cross section by adjusting a size of said aperture of said radiation diaphragm.

6. A method as claimed in claim 5 comprising continuously modifying said beam cross section from detector row-to-detector row.

7. A method as claimed in claim 4 comprising discretely modifying said beam cross section detector row-by-detector row.

8. A method as claimed in claim 4 wherein the step of conducting a scan comprises relatively displacing said focus of said X-ray source and said examination subject along said system axis, in a displacement direction, while rotating at least said focus of said X-ray source around said system axis, to conduct a spiral scan of said examination subject, and wherein said detector system contains a detector row which is farthest back in said displacement direction, and, at a beginning of said spiral scan, fading in only said detector row which farthest back in said displacement direction, and subsequently fading in additional rows of said detector system row-by-row while relatively displacing said focus and said examination subject in said displacement direction.

9. A method as claimed in claim 8 wherein said computed tomography device has a pitch, and comprising fading in a plurality of said detector rows, dependent on said pitch, during each complete revolution of said focus around said system axis.

10. A method as claimed in claim 11 comprising fading in a plurality of said detector rows during each complete revolution of said focus around said system axis which increases as said pitch increases.

11. A method as claimed in claim 10 comprising fading in a plurality of said detector rows during each complete revolution of said focus around said system axis which is equal in number to said pitch.

12. A method as claimed in claim 4 wherein the step of conducting a scan comprises relatively displacing said focus of said X-ray source and said examination subject along said system axis, in a displacement direction, while rotating at least said focus of said X-ray source around said system axis, to conduct a spiral scan of said examination subject, and wherein said detector system contains a detector row which is farthest back in said displacement direction, and, at an end of said spiral scan, blanking out only said detector row which farthest back in said displacement direction, and subsequently blanking out additional rows of said detector system row-by-row while relatively displacing said focus and said examination subject in said displacement direction.

13. A method as claimed in claim 12 wherein said computed tomography device has a pitch, and comprising blanking out a plurality of said detector rows, dependent on said pitch, during each complete revolution of said focus around said system axis.

14. A method as claimed in claim 13 comprising blanking out a plurality of said detector rows during each complete revolution of said focus around said system axis which increases as said pitch increases.

15. A method as claimed in claim 14 comprising blanking out a plurality of said detector rows during each complete revolution of said focus around said system axis which is equal in number to said pitch.

16. A method as claimed in claim 4 wherein said X-ray beam has a finite size on said detector system and comprising blanking out selected detector rows of said detector system so that all detector rows of said detector system which are not blanked out have said X-ray beam incident thereon.

17. A method as claimed in claim 1 wherein the step of modifying said beam cross section comprises at least one of blanking out a plurality of detector rows from having said x-ray beam incident thereon during said scan and fading in a plurality of detector rows to have said X-ray beam incident thereon during said scan.

18. A computed tomography device, having a system axis, for scanning an examination subject comprising:

an X-ray source with a focus from which an X-ray beam, having a beam cross section, emanates;

a detector system having a plurality of detector rows, each detector row containing a plurality of detector elements;

a scanner containing said X-ray source and said detector system for conducting a scan of said examination subject by displacing at least said focus of said X-ray source relative to said system axis to irradiate said examination subject with said X-ray beam from a plurality of different positions relative to said system axis, said detector system generating detector signals corresponding to radiation incident on said detector system during said scan;

a computer supplied with said signals for reconstructing an image of said examination subject from said detector signals; and a beam modifier for modifying said cross section of said X-ray beam during said scan so that, at all times, substantially only a region of said examination subject which is used for reconstructing said image is penetrated by said X-ray beam.

19. A computed tomography device as claimed in claim 18 wherein said computed tomography device has a system axis, and wherein each of said detector rows has an equal extent along said system axis.

* * * * *